US008168842B2

(12) United States Patent
Chewter et al.

(10) Patent No.: US 8,168,842 B2
(45) Date of Patent: May 1, 2012

(54) PROCESS FOR THE ALKYLATION OF A CYCLOALKENE

(75) Inventors: Leslie Andrew Chewter, Amsterdam (NL); Aden Murphy, Amsterdam (NL); Michiel Johannes Franciscus Maria Verhaak, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 64 days.

(21) Appl. No.: 12/301,159

(22) PCT Filed: May 16, 2007

(86) PCT No.: PCT/EP2007/054745
§ 371 (c)(1),
(2), (4) Date: Feb. 24, 2009

(87) PCT Pub. No.: WO2007/135047
PCT Pub. Date: Nov. 29, 2007

(65) Prior Publication Data
US 2009/0227824 A1 Sep. 10, 2009

(30) Foreign Application Priority Data

May 19, 2006 (EP) .................................. 06114276

(51) Int. Cl.
*C07C 2/86* (2006.01)
(52) U.S. Cl. ........ 585/375; 585/317; 585/318; 585/376; 585/643
(58) Field of Classification Search .................. 585/643, 585/375, 317, 318, 376
See application file for complete search history.

(56) References Cited

U.S. PATENT DOCUMENTS

| | | | |
|---|---|---|---|
| 679,851 A | 8/1901 | Leckband | |
| 1,351,424 A | 8/1920 | Jenkins | |
| 2,402,863 A | 6/1946 | Zuidema et al. | 44/62 |
| 2,593,446 A | 4/1952 | Heinemann | 260/666 |
| 2,765,355 A | 10/1956 | Nozaki | 260/666 |
| 3,906,054 A * | 9/1975 | Kaeding et al. | 585/711 |
| 4,076,796 A | 2/1978 | Reh et al. | 423/659 |
| 4,076,842 A | 2/1978 | Plank et al. | 423/328 |
| 4,151,214 A | 4/1979 | Kim et al. | 260/676 |
| 4,197,185 A | 4/1980 | Le Page et al. | 208/71 |
| 4,243,828 A | 1/1981 | Kerr et al. | 585/467 |
| 4,397,827 A | 8/1983 | Chu | 423/326 |
| 4,537,754 A | 8/1985 | Casci et al. | 423/277 |
| 4,544,792 A | 10/1985 | Smith et al. | 585/533 |
| 4,556,477 A | 12/1985 | Dwyer | 208/111 |
| 4,590,320 A | 5/1986 | Sapre | 585/324 |
| 4,626,415 A | 12/1986 | Tabak | 422/190 |
| 4,665,249 A | 5/1987 | Mao et al. | 585/408 |
| 4,684,757 A | 8/1987 | Avidan et al. | 585/331 |
| 4,814,532 A * | 3/1989 | Yoshida et al. | 585/357 |
| 5,043,503 A * | 8/1991 | Del Rossi et al. | 585/360 |
| 5,210,364 A * | 5/1993 | Barri et al. | 585/640 |
| 5,302,762 A | 4/1994 | Yamashita et al. | 568/895 |
| 5,367,100 A | 11/1994 | Gongwei et al. | 585/640 |
| 5,817,906 A | 10/1998 | Marker et al. | 585/640 |
| 6,046,372 A | 4/2000 | Brown et al. | 585/640 |
| 6,100,435 A * | 8/2000 | Silverberg et al. | 585/318 |
| 6,264,799 B1 | 7/2001 | Stiwe et al. | 203/78 |
| 6,307,117 B1 | 10/2001 | Tsunoda et al. | 585/651 |
| 6,339,181 B1 | 1/2002 | Chen et al. | 585/653 |
| 6,372,949 B1 | 4/2002 | Brown et al. | 585/639 |
| 6,468,399 B2 * | 10/2002 | Stuwe et al. | 203/71 |
| 6,656,345 B1 | 12/2003 | Chen et al. | 208/120.01 |
| 6,791,002 B1 | 9/2004 | Abrevaya et al. | 585/648 |
| 6,797,851 B2 | 9/2004 | Martens et al. | 585/640 |
| 2002/0063082 A1 | 5/2002 | Touvelle et al. | 208/134 |
| 2003/0078463 A1 | 4/2003 | Martens et al. | 585/638 |
| 2003/0125598 A1 | 7/2003 | Chisholm et al. | 585/640 |
| 2003/0181777 A1 | 9/2003 | Powers et al. | 585/648 |
| 2004/0015028 A1 | 1/2004 | Brown et al. | 585/520 |
| 2006/0020155 A1 | 1/2006 | Beech, Jr. et al. | 585/639 |
| 2006/0135834 A1 | 6/2006 | Xu et al. | 585/639 |
| 2009/0105429 A1 | 4/2009 | Chewter et al. | 526/67 |
| 2009/0170739 A1 * | 7/2009 | Miller | 508/591 |

FOREIGN PATENT DOCUMENTS

| | | |
|---|---|---|
| DE | 10027159 | 12/2001 |
| DE | 10043644 | 3/2002 |
| EP | 0088494 | 1/1983 |
| EP | 109059 | 5/1984 |
| EP | 162475 | 11/1985 |
| EP | 0340576 | 11/1989 |
| EP | 0343454 | 11/1989 |
| EP | 0489497 | 11/1991 |
| EP | 0485145 | 5/1992 |
| EP | 0489497 | 6/1992 |
| EP | 0596256 | 5/1994 |
| EP | 0788838 | 10/1995 |
| EP | 921181 | 6/1999 |
| GB | 663901 | 12/1951 |
| JP | 58194828 | 11/1983 |
| JP | 61249945 | 11/1986 |

(Continued)

OTHER PUBLICATIONS

IZA-Structure Data, "Database of Zeolite Structures" at www.iza-strucutre.org available on-line on Aug. 25, 2010.*
IZA-Structure Data, "Database of Zeolite Structures" at www.iza-structure.org available on-line on Aug. 25, 2010.*
Meier, et al: Atlas of zeolite structure types passage, 2001, pp. 9-20.
Laborchemikalien and Analytische Reagenzien, 2005, Fluka Riedel-De Haeen, p. 1190.
International Search Report (PCT/EP2007/054745).
Weissermehl, K., et al., Industrial Organic Chemistry, $3^{rd}$ Edition, Wiley, 1997, pp. 13-28.
Ch. Baerlocher, et al., Database of Zeolite Structures: http://www.iza-structure.org/databases/.

*Primary Examiner* — In Suk Bullock
*Assistant Examiner* — Bradley Etherton

(57) ABSTRACT

Process for the alkylation of a cycloalkene, which process comprises alkylating a cycloalkene with an oxygenate under alkylating conditions in the presence of a zeolite; to yield an alkylated cycloalkene. Composition obtainable by such a process and use of such a composition as a gasoline blending component.

7 Claims, No Drawings

FOREIGN PATENT DOCUMENTS

| | | |
|---|---|---|
| JP | 63154636 | 6/1988 |
| JP | 9030999 | 2/1997 |
| JP | 9302359 | 11/1997 |
| JP | 10036295 | 2/1998 |
| SU | 695997 | 11/1979 |
| WO | WO9302994 | 2/1993 |
| WO | WO9522516 | 8/1995 |
| WO | WO9957085 | 11/1999 |
| WO | WO9957226 | 11/1999 |
| WO | WO0026163 | 5/2000 |
| WO | WO0029358 | 5/2000 |
| WO | WO0123500 | 4/2001 |
| WO | WO0129152 | 4/2001 |
| WO | WO0134730 | 5/2001 |
| WO | WO0162689 | 8/2001 |
| WO | WO0181280 | 11/2001 |
| WO | WO0185872 | 11/2001 |
| WO | WO0190279 | 11/2001 |
| WO | WO0210098 | 2/2002 |
| WO | WO02079135 | 10/2002 |
| WO | WO03020667 | 3/2003 |
| WO | WO2004018089 | 3/2004 |
| WO | WO2004018392 | 3/2004 |
| WO | WO2004031327 | 4/2004 |
| WO | WO2004037950 | 5/2004 |
| WO | WO2004056944 | 7/2004 |
| WO | WO2005016856 | 2/2005 |
| WO | WO2005028594 | 3/2005 |
| WO | WO2006020083 | 2/2006 |
| WO | WO2007135052 | 11/2007 |

* cited by examiner

PROCESS FOR THE ALKYLATION OF A CYCLOALKENE

PRIORITY CLAIM

The present application claims priority to European Patent Application 06114276.6 filed 19 May 2006.

TECHNICAL FIELD OF THE INVENTION

This invention relates to a process for the alkylation of a cycloalkene, more in specific the invention relates to a process for the preparation of alkylated cyclopentene, cyclohexene, vinylcyclohexene or ethylcyclohexene.

BACKGROUND OF THE INVENTION

Organic compounds comprising a cycloalkene ring substituted with one or more alkyl groups, such as for example alkylcyclopentenes, dialkylcyclopentenes, alkylcyclohexenes, dialkylcyclohexenes, trialkylcyclo-hexenes and alkylated alkenyl-cyclohexenes are desirable chemicals.

For example 1-methylcyclopentene, 1-methylcyclo-hexene, 1,2-dimethylcyclohexene, 1,2,4-trimethyl-4-isopropenyl-cyclohexene, are interesting gasoline blending components, as described for example in U.S. Pat. No. 2,402,863 and JP-A-09302359 and the article "Knocking Characteristics of Pure Hydrocarbons" by the American Petroleum Institute, ASTM Special Technical Publication No. 225, 1958, page 14.

In addition, such compounds comprising a cycloalkene ring substituted with one or more alkyl groups have application as starting component for various other organic compounds. For example, methylcyclopentene and/or methylcyclohexene can be used in for example the synthesis of various insecticides, resin intermediates and related products. If desirable, methylcyclopentene can be isomerized into cyclohexene or hydrogenated and isomerized into cyclohexane. Such a process can be useful if at a certain location less cyclohexane than desired is available.

If desirable, cyclohexane can, in turn, be converted to benzene. Also methylcyclopentene can be converted to benzene over a conventional reformer catalyst.

Processes for the preparation of e.g. alkylcycloalkene and/or dialkylcycloalkene are well known in the art.

For example, U.S. Pat. No. 2,593,446, U.S. Pat. No. 2,765,355 and JP-A-10036295 describe the preparation of methylcyclopentene by selective dehydrogenation of methylcyclopentane.

Such dehydrogenation, however, has several disadvantages. It is an endothermic reaction, which requires energy to be added to the process. Dehydrogenation must also be carried out at a low partial pressure in order to favor the production of olefins.

Furthermore, it is difficult to fully control the dehydrogenation. Therefore the dehydrogenation often generates less desirable by-products such as less desirable stereoisomers, di-olefins and benzene. Such di-olefins can cause fouling in a reactor under dehydrogenation conditions. Such fouling can result in considerable coke-formation.

The dehydrogenation of methylcyclopentane, for example, produces not only 1-methylcyclopentene, but also its stereoisomers such as 4-methylcyclopentene. As is clear from the above-mentioned article "Knocking Characteristics of Pure Hydrocarbons", the latter is a less desirable gasoline blending component. A further disadvantage, specifically for the preparation of methylcyclopentene via dehydrogenation, is that the starting compound for such dehydrogenation, i.e. methylcyclopentane, is difficult to obtain in a relatively pure form by distillation. Methylcyclopentane is often obtained as a part of a C6 fraction of a gasoline, for example a fully hydrotreated pyrolysis gasoline, comprising also compounds such as n-hexane or cyclohexane. Methylcyclopentane has a boiling point of about 71° C., whereas for example n-hexane has a boiling point of about 69° C. The methylcyclopentane is, therefore, difficult to separate as a pure component through simple distillation from such n-hexane.

It would therefore be desirable to have an alternative process for the preparation of organic compounds comprising a cycloalkene ring substituted with one or more alkyl groups. It would further be desirable if such alternative process could be based on an exothermic reaction and would produce only a limited amount of undesirable byproducts such as benzene.

U.S. Pat. No. 4,151,214 describes a method comprising reacting an olefin with methanol and a catalytically effective amount of a metal halide selected from $ZnI_2$, $ZnBr_2$, and mixtures thereof at a temperature of from 190° C. to 300° C. In example 6, U.S. Pat. No. 4,151,214 describes the reaction of cyclohexene, methanol and Zinc Iodide at a temperature of 200° C. This process has, however, the disadvantage that the conversion and selectivity for the reaction are very low. The product stream in example 6 contained 77.7% unreacted cyclohexene, 6.2% methyl cyclohexenes and 3.2% dimethyl cyclohexenes.

It would be desirable to have a process for the alkylation of a cycloalkene with an oxygenate, which has a high conversion and/or selectivity.

SUMMARY OF THE INVENTION

It has now been surprisingly found that cycloalkenes can be alkylated by an oxygenate with high conversion and selectivity in the presence of a zeolite.

Accordingly the present invention provides a process for the alkylation of a cycloalkene, which process comprises alkylating a cycloalkene with an oxygenate under alkylating conditions in the presence of a zeolite; to yield an alkylated cycloalkene.

The process according to the invention results in advantageously high conversions and selectivities towards the desired alkylated cycloalkene. In addition, the reaction of the cycloalkene ring with the oxygenate in such a process is exothermic, i.e. generating energy, and is therefore economically more advantageous than the former mentioned dehydrogenation. The process can also, if desired, be carried out at normal pressure (about 1 atmosphere). Furthermore, the amount of byproducts such as benzene, is low.

In addition, specifically for the preparation of methyl-cyclopentene, a starting compound such as cyclopentene can be easily obtained from a $C_5$ fraction of a gasoline such as a pyrolysis gasoline by simple distillation. This is for example illustrated in U.S. Pat. No. 6,264,799.

DETAILED DESCRIPTION OF THE INVENTION

The cycloalkene used as starting compound can be any cycloalkene or cycloalkene derivative. That is, such cycloalkene can be any organic starting compound, comprising a cycloalkene ring. The cycloalkene, which is used as a starting compound in the process of the invention is hereafter sometimes also referred to as organic starting compound, starting compound or cycloalkene starting compound.

The cycloalkene contains at least one cycloalkene ring, optionally being substituted with one or more substituents. By alkylation of the cycloalkene is understood that such cycloalkene ring is alkylated.

Preferably the cycloalkene contains only one cycloalkene ring. Such a cycloalkene ring can be substituted or non-substituted. When substituted, the cycloalkene ring can be substituted with one or more substituents, preferably 1 to 3 substitutents. The substituents are preferably hydrocarbyl groups.

Hence, in a first preferred embodiment the cycloalkene, used as a starting compound, is a cycloalkene, comprising a cycloalkene ring, which ring is non-substituted. In such case the cycloalkene starting compound consists of only a cycloalkene ring.

In a second preferred embodiment the cycloalkene, used as a starting compound, is a cycloalkene, comprising a cycloalkene ring, which ring is substituted with one or more hydrocarbyl groups.

If substituted with any hydrocarbyl groups, the cycloalkene is preferably substituted with 1 to 3, more preferably 1 or 2 hydrocarbyl groups. Such hydrocarbyl groups are preferably alkyl and/or alkenyl groups. Such alkyl and/or alkenyl groups preferably have from 1 to 4 carbon atoms. Preferred hydrocarbyl groups therefore include $C_1$-$C_4$ alkyl groups, such as methyl, ethyl, propyl, isopropyl, butyl and tert-butyl, and $C_1$-$C_4$ alkenyl groups, such as vinyl, propenyl, isopropenyl, butenyl and iso-butenyl. Most preferably the cycloalkene is a non-substituted cycloalkene or a cycloalkene substituted with one or two $C_1$-$C_4$ alkyl groups.

The cycloalkene preferably has a cycloalkene ring having from 4 to 6 carbons in the ring. More preferably the cycloalkene comprises a cyclopentene or cyclohexene ring. Still more preferably the cycloalkene is a substituted or non-substituted cyclopentene or a substituted or non-substituted cyclohexene.

Examples of cycloalkenes especially suitable as organic starting compounds in the process include cyclopentene, methylcyclopentenes (especially 1-methylcyclopentene and 4-methylcyclopentene), ethylcyclopentenes, dimethylcyclopentenes, cyclohexene, methylcyclohexenes (especially 1-methylcyclohexene and 4-methylcyclohexene) ethylcyclohexenes, (specifically 4-ethylcyclohexene), dimethylcyclohexenes and 4-vinylcyclohexene.

In the process according to the invention the cycloalkene, comprising a cycloalkene ring, is converted (i.e. alkylated) into an alkylated cycloalkene. In the alkylated cycloalkene, the cycloalkene ring is substituted with one or more alkyl groups. The alkylated cycloalkene can be any alkylated cycloalkene or alkylated cycloalkene derivative. That is, the alkylated cycloalkene can be any organic product compound, comprising a cycloalkene ring, wherein such ring has been substituted with one or more alkyl groups by alkylation. The alkylated cycloalkene is hereafter sometimes also referred to as organic product compound, product compound or alkylated cycloalkene product compound.

If the cycloalkene used as starting compound was already substituted with an alkyl group, the process results in the cycloalkene being substituted with one or more additional alkyl groups.

Preferably the cycloalkene is alkylated to become substituted with 1 to 3, possibly additional, alkyl groups.

More preferably the cycloalkene becomes substituted with one or two alkyl groups, in order to prepare the corresponding alkylated or di-alkylated organic compound. By an alkyl group is understood an organic group that is saturated, (i.e. comprises no double or triple bonds), and consists of only hydrogen and carbon atoms (i.e. comprises no heteroatoms).

The alkyl groups are preferably alkyl groups having from 1 to 4 carbon atoms. Examples of such alkyl groups include methyl, ethyl, propyl, isopropyl, butyl, isobutyl and tert-butyl groups. Most preferably the alkylated cycloalkene is substituted with methyl and/or ethyl groups.

Alkylated cycloalkene product compounds that can be prepared with the process of the invention include for example 1-alkylcyclopentene; 1,2-dialkylcyclopentene; 1-alkylcyclohexene; 1,2 dialkylcyclohexene; 1- and/or 2-alkyl-methylcyclopentenes; 1- and/or 2-alkyl methylcyclohexenes (such as for example 1-alkyl-4-methyl-cyclohexene, 1,2 dialkyl 4-methyl-cyclohexene); 1-alkyl-4-methyl-4-isopropenyl-cyclohexene; 1-alkyl-4-vinylcyclopentene; 1-alkyl-ethylcyclohexenes; 1,2-dialkyl-ethylcyclohexenes; 1-alkyl-alkenylcyclo-hexenes (such as 1-alkyl-vinylcyclohexenes); 1,2-dialkyl-alkenylcyclohexenes (such as 1,2-dialkyl-vinyl-cyclo-hexenes);

Most preferably the cycloalkene starting compound is cyclopentene, cyclohexene, ethylcyclohexene or vinyl-cyclohexene, in order to prepare an alkylated cyclopentene, an alkylated cyclohexene, an alkylated ethylcyclohexene or an alkylated vinyl-cyclohexene.

Examples of such alkylated cyclopentene, alkylated cyclohexene, alkylated ethylcyclohexene or alkylated vinyl-cyclohexene that can be prepared include methylcyclopentene; dimethylcyclopentene; ethylcyclopentene; diethylcyclopentene; methylethylcyclopentene; methylcyclohexene; dimethylcyclohexene; ethylcyclohexene; diethylcyclohexene; methylethylcyclohexene; triethylcyclohexene; dimethylethylcyclohexene; diethylmethylcyclohexene; methylvinylcyclohexene; methylpropenylcyclohexene; dimethylvinylcyclohexene; dimethylpropenylcyclohexene; and ethylvinylcyclohexene; diethylvinylcyclohexene; methylethylvinylcyclohexene; and mixtures thereof. In a preferred embodiment the cycloalkene starting compound is alkylated with one or more methyl groups, preferably one or two methyl groups. Preferred examples of alkylated cycloalkene product compounds therefore include 1-methylcyclopentene; 1,2-dimethyl-cyclopentene; 1-methyl-ethylcyclohexene; 1,2 dimethyl-cyclohexene; 1,4 dimethylcyclohexene; 1,2,4-trimethylcyclohexene and 1,2,4-trimethyl-4-isopropenylcyclohexene; 1-methyl-4-vinylcyclopentene; 1,2-dimethyl-4-vinylcyclohexene; 1-methyl-ethylcyclohexene and 1,2-dimethyl-4-ethylcyclohexene.

Most preferably cyclopentene or ethylcyclohexene is used as a starting compound and alkylated by the process according to the invention into a cyclopentene or ethylcyclohexene with methyl and/or (further) ethyl groups.

The process can be carried out with a suitable organic starting compound from any source known to the skilled person.

If desirable, a starting compound such as cyclohexene can for example also be prepared through isomerization of methylcyclopentene.

If 4-vinyl-cyclohexene is used as a starting compound, such 4-vinyl-cyclohexene can conveniently be obtained from a dimerisation of 1,3-butadiene.

If 4-ethyl-cyclohexene is used as a starting compound, such 4-ethyl-cyclohexene can conveniently be obtained via a hydrogenation of 4-vinyl-cyclohexene.

In a preferred embodiment the cycloalkene, used as a starting compound is derived from a distillation fraction of a pyrolysis gasoline. In a steam cracker feeds such as for example naphtha (boiling e.g. between 25° C. and 180° C., preferably boiling between 30° C. and 160° C., more preferably boiling between 35° C. and 150° C.), gasoil (boiling e.g. between 120° C. and 370° C., preferably boiling between 150° C. and 300° C., more preferably boiling between 180° C. and 250° C.) and hydrowax or vacuum gasoil (boiling e.g. between 200° C. and 700° C., more preferably between 250° C. and 600° C.) are converted into lighter products.

The product stream can be distilled into several fractions. By a pyrolysis gasoline is understood a distillation fraction, boiling between C5-205° C., preferably between 25° C. and 180° C., obtained after distillation of the product stream of such a steam cracker, such as for example illustrated in the Petroleum Handbook, 6th edition, compiled by the staff of the Royal Dutch/shell Group of Companies, published by Elsevier (1983), page 309.

The pyrolysis gasoline can be split into several product streams by for example distillation, extraction or other separation methods. The cycloalkene starting compound can be derived from such product streams.

Cyclopentene can for example be recovered from a $C_5$ distillation fraction by converting any cyclopentadienes through dimerisation to dicyclopentadiene, followed by separation through distillation and subsequent cracking of the bottom product, dicyclopentadiene, back to cyclopentadiene. Such a process is for example described in Industrial Organic Chemistry 3rd ed. By K. Weissermerl and, H.-J. Arpe VCH ISBN 3-527-28838-4 p. 123-124.

The cyclopentadiene can subsequently be partially hydrogenated to cyclopentene.

By partial hydrogenation is understood a hydrogenation under hydrogenation conditions wherein less than all olefins are hydrogenated, i.e. wherein the resultant concentration of olefins is 0.5% w/w or more. Preferably the partial hydrogenation is carried out such that more than 90% w/w, preferably more than 95% w/w and most preferably 100% w/w of the di-olefins present are converted into mono-olefins or, preferably only to limited extent, paraffins, whilst hydrogenation of the mono-olefins is kept as low as possible. Most preferably the $C_5$ stream is hydrogenated to such an extent that the di-olefin concentration after the hydrogenation step is below 0.5% w/w based on the total composition.

Such a hydrogenation can be carried out in any manner known by the skilled person to be suitable for this purpose. Such a hydrogenation process is for example described in the Handbook of petroleum refining processes 2nd edition by Robert A. Meyers, published by Mc Graw Hill (1997) pages 8.27 and 8.28; and in the Petroleum Handbook, 6th edition, compiled by the staff of the Royal Dutch/shell Group of Companies, published by Elsevier (1983), pages 309-311. A suitable hydrogenation process is for example further described in WO-A-2005/028594 under the section selective hydrogenation.

Another process for the recovery of cyclopentene is described in WO 00/29358.

In a specific preferred embodiment a $C_5$ distillation fraction of a pyrolysis gasoline is partially hydrogenated, for example over a hydrogenation catalyst comprising a Group VIII metal such as Pt or Ni and at a hydrogenation temperature in the range from 50° C. to 150° C.;

whereafter it is catalytically cracked, for example over a zeolite; whereafter organic compounds comprising an cyclopentene ring in the resultant product are alkylated according to the process described herein. The alkylated cyclopentenes can subsequently be easily separated, for example by distillation, from the remaining saturated $C_5$ compounds in the mixture.

The partial hydrogenation and cracking of the $C_5$-distillation fraction can result in a stream containing concentrations of cyclopentene of 10-35 wt %.

As indicated before, cyclopentene can also easily be obtained in a relatively pure form from a $C_5$ fraction by simple distillation as for example illustrated in U.S. Pat. No. 6,264,799. The therein described distillation can for example be used for obtaining relatively pure cyclpentene from a $C_5$-product obtained via a dicyclopentadiene process as described above, or from a $C_5$-product obtained via a partially hydrogenation of a $C_5$ distillation fraction.

In addition to cyclopentene also other cycloalkenes, suitable as starting compound, such as methylcyclopentene and dimethylcyclopentene can be obtained from the above described pyrolysis gasoline distillation fractions.

The cycloalkene starting compound can be a part of an organic feed, which is to be contacted with the oxygenate in the process of the invention. Such an organic feed can comprise just one cycloalkene or a mixture of cycloalkenes. Furthermore the organic feed of the process can comprise other compounds in addition to any cycloalkenes(s).

In one preferred embodiment an organic feed to be contacted with the oxygenate consists mainly of a cycloalkene or mixture of cycloalkenes, that is, it preferably comprises at least 80% wt of cycloalkene(s), more preferably at least 90% wt of cycloalkene(s), still more preferably at least 95% wt of cycloalkene(s) and most preferably between 98% wt and 100% wt of cycloalkene(s).

In another preferred embodiment the organic feed comprises other compounds in admixture with the cycloalkene. Such other compounds can, for example be saturated organic compounds such as alkanes. For example a partly hydrogenated C5-distillation fraction of a pyrolysis gasoline, comprising for example also cyclopentane and/or pentane in addition to any cyclopentene, can be fed directly into the process of the invention. Preferably such a organic feed comprising a mixture of cycloalkene(s) and other compounds comprises at least 15% wt of cycloalkene(s), more preferably at least 30% wt of cycloalkene(s), still more preferably at least 50% wt of cycloalkene(s), most preferably in the range from 70% wt to 80% wt of cycloalkene(s).

By an oxygenate is understood a compound obtainable by oxidation of a hydrocarbon. Water is therefore not understood to be an oxygenate. Examples of oxygenates include alcohols, such as methanol, ethanol, isopropanol, ethylene glycol, propylene glycol; ketones, such as acetone and methylethylketone; aldehydes, such as formaldehyde, acetaldehyde and propionaldehyde; ethers, such as dimethylether, diethylether, methylethylether, tetrahydrofuran and dioxane; epoxides such as ethylene oxide and propylene oxide; and acids, such as acetic acid, propionic acid, formic acid and butyric acid. Of these alcohols and ethers are preferred.

The oxygenate used in the process according to the invention is preferably an oxygenate which comprises at least one oxygen-bound C1-C4 alkyl group. The oxygenate can comprise one or more oxygen-bound C1-C4 alkyl group. Preferably the oxygenate comprises one or two C1-C4 alkyl groups. Preferably such oxygenate comprising at least one oxygen-bound C1-C4 alkyl group is chosen from the group of ethers, such as dimethylether, diethylether, methylethylether; and alcohols, such as methanol, ethanol, isopropanol.

More preferably a oxygenate is used having at least one oxygen bound C1 or C2 alkyl group. Most preferably the oxygenate is methanol, ethanol, diethylether or dimethylether.

In a preferred embodiment, where the oxygenate is methanol, such methanol is obtained from natural gas. For example by a process as described in Industrial Organic Chemistry 3rd edition page 28.

In another preferred embodiment the oxygenate is obtained through fermentation of biomaterials. For example by a process as described DE-A-10043644.

The preferred molar ratio of oxygenate to cycloalkene depends on the specific oxygenate used and the number of reactive oxygen-bonded alkyl groups therein. Preferably the ratio of mol reactive oxygen-bonded alkyl groups to mol cycloalkene lies in the range of 10:1 to 1:10, more preferably in the range of 5:1 to 1:5 and still more preferably in the range of 2:1 to 1:2.

In a preferred embodiment wherein the oxygenate comprises only one oxygen-bonded alkyl group, such as for example methanol or ethanol, the molar ratio preferably lies in the range from 5:1 to 1:5 and more preferably in the range of 2:1 to 1:2. Most preferably the molar ratio in such a case is about 1:1.

In another preferred embodiment wherein the oxygenate comprises two oxygen-bonded alkyl group, such as for example dimethylether, the molar ratio preferably lies in the range from 5:2 to 1:10 and more preferably in the range of 1:1 to 1:4. Most preferably the molar ratio in such a case is about 1:2.

The process is carried out in presence of zeolite. Preferably, this zeolite is zeolite comprising a 10-membered ring channel. More preferably this zeolite is a one-dimensional zeolite having 10-membered ring channels.

These are understood to be zeolites having only 10-membered ring channels in one direction which are not intersected by other 8, 10 or 12-membered ring channels.

One suitable zeolite is a zeolite of the MFI-type (for example ZSM-5). Preferably, however, the zeolite is selected from the group of TON-type (for example ZSM-22), MTT-type (for example ZSM-23), STF-type (for example SSZ-35), SFF-type (for example SSZ-44 and EU-2/ZSM 48, EUO type (for example ZSM-50) and EU-2.zsm 48 zeolites.

These zeolites are distinct from other zeolites having small pore 8-ring channels or zeolites having large pore 12-ring channels.

MTT-type catalysts are more particularly described in e.g. U.S. Pat. No. 4,076,842. For purposes of the present invention, MTT is considered to include its isotypes, e.g., ZSM-23, EU-13, ISI-4 and KZ-1.

TON-type zeolites are more particularly described in e.g. U.S. Pat. No. 4,556,477. For purposes of the present invention, TON is considered to include its isotypes, e.g., ZSM-22, Theta-1, ISI-1, KZ-2 and NU-10.

EU-2-type zeolites are more particularly described in e.g. U.S. Pat. No. 4,397,827. For purposes of the present invention, EU-2 is considered to include its isotypes, e.g., ZSM-48. EUO-type zeolites are more particularly described in U.S. Pat. No. 4,537,754. For purposes of the present invention, EUO is considered to include its isotypes, e.g., ZSM-50, EU-1 and TPZ-3.

In a further preferred embodiment a zeolite of the MTT-type, such as ZSM-23, or a TON-type, such as ZSM-22 is used. A zeolite of the MTT-type was found especially advantageous, as it results in a very low amount of benzene-byproducts.

Preferably a zeolite in the hydrogen form is used, e.g., HZSM-22, HZSM-23, H-ZSM-35 and HZSM-48 and HZSM-50. Preferably at least 50% w/w, more preferably at least 90% w/w, still more preferably at least 95% w/w and most preferably 100% of the total amount of zeolite used is zeolite in the hydrogen form. When the zeolites are prepared in the presence of organic cations the zeolite may be activated by heating in an inert or oxidative atmosphere to remove the organic cations, for example, by heating at a temperature over 500° C. for 1 hour or more. The hydrogen form can then be obtained by an ion exchange procedure with ammonium salts followed by another heat treatment, for example in an inert or oxidative atmosphere at a temperature over 500° C. for 1 hour or more. The latter zeolites are also referred to as being in the ammonium form.

The zeolite has a silica to alumina ratio (SAR) in the range from 1 to 500. Preferably the zeolite has a SAR in the range from 10 to 200. In a further preferred embodiment, when a zeolite with a high stability is desired, a zeolite having a SAR in the range from 80 to 200 is preferred. In another preferred embodiment, when a zeolite with a high activity is desired, a zeolite with a SAR in the range from 20 to 100 is preferred.

The zeolite can be used as such or in combination with a so-called binder material. When used in the reaction, the zeolite as such or the zeolite in combination with a binder material, are hereafter also referred to as zeolite catalyst.

It is desirable to provide a catalyst having good mechanical strength, because in an industrial environment the catalyst is often subjected to rough handling, which tends to break down the catalyst into powder-like material. The later causes problems in the processing. Preferably the zeolite is therefore incorporated in a binder material. Examples of suitable binder materials include active and inactive materials and synthetic or naturally occurring zeolites as well as inorganic materials such as clays, silica, alumina, aluminosilicate. For present purposes, inactive materials of a low acidity, such as silica, are preferred because they may prevent unwanted side reactions which may take place in case a more acidic material, such as alumina is used. Preferably the catalyst used in the process of the present invention comprises, in addition to the zeolite, 2 to 90 wt %, preferably 10 to 85 wt % of a binder material.

The process of the present invention can be carried out in a batch, continuous, semi-batch or semi-continuous manner using conventional reactor systems such as fixed bed, moving bed, fluidized bed and the like. As a reactor any reactor known to the skilled person to be suitable for catalytic cracking can be used.

Conventional catalyst regeneration techniques can be employed. The catalyst used in the process of the present invention can have any shape known to the skilled person to be suitable for this purpose, for example the catalyst can be present in the form of catalyst tablets, rings, extrudates, etc. extruded catalysts can be applied in various shapes, such as, cylinders and trilobes. If desired, spent catalyst can be regenerated and recycled to the process of the invention.

The process according to the invention is carried out under alkylating conditions. By alkylating conditions is understood any reaction conditions known to the skilled person to be effective in alkylation reactions. The process can be carried out over a wide range of temperatures and pressures. Preferably, however, the hydrocarbon feed is contacted with the zeolite catalyst at a temperature in the range from 200° C. to 500° C., more preferably in the range from 250° C. to 500° C., still more preferably in the range from 250° C. to 450° C. and most preferably in the range from above 300° C. to 450° C.; and at an absolute pressure in the range from 0.5 to 10 bar, more preferably 1 to 5 bar, still more preferably in the range from 1 to 3 bar.

Preferably the cycloalkene(s) and the oxygenate are fed to the process according to the invention as a vapour, preferably diluted with a diluent gas. Preferably such a diluent gas is an inert gas, such as for example nitrogen or argon. For example, the oxygenate feed and/or olefinic co-feed can be diluted with steam, for example in the range from 0.01 to 10 kg steam per kg feed. In some cases also a hydrocarbon diluent might be used, such as for example a saturated C4 and/or C5 stream.

In a further preferred embodiment small amounts of water are added in order to improve the stability of the catalyst by reducing coke formation.

The alkylated cycloalkene or product composition containing alkylated cycloalkene obtainable by the process can be useful as a gasoline blending component (as described for example in U.S. Pat. No. 2,402,863 and JP-A-09302359 and the article "Knocking Characteristics of Pure Hydrocarbons" by the American Petroleum Institute, ASTM Special Technical Publication No. 225, 1958, page 14). They can be especially advantageous when blended with a low RON base fuel, i.e. a base fuel having a RON of below 85. Especially compositions containing high amounts of 1-methylcycloalkenes, preferably at least 10 wt %, more preferably at least 20 wt % of 1-methylcycloalkenes, and low amounts of benzene, preferably less than 2 wt %, more preferably less than 1 wt % of benzene, are advantageous as explained before. As exemplified below the present process can generate such compositions.

The invention will hereinbelow be further illustrated by the following non-limiting examples.

EXAMPLE 1

In this example cyclopentene (CP) and dimethylether (DME) were reacted in a molar feed ratio CP:DME of 2:1 over an MFI-type and an MTT-type zeolite. The silica-to-alumina ratio were 280 and 48 for the MFI-type and the MTT-type zeolite, respectively. A sample of zeolite powder was pressed into tablets and the tablets were broken into pieces and sieved. For catalytic testing, the sieve fraction of 30-80 mesh has been used. A quartz reactor tube of 3 mm internal diameter was loaded with 200 mg of sieve fraction. Prior to reaction, the fresh catalyst in its ammonium-form was treated with flowing argon at 550° C. for 1 hour. Next, the catalyst was cooled in argon to the reaction temperature and a mixture consisting of 2.0 vol. % cyclopentene, 1.1 vol. % dimethylether and 1 vol. % of water in argon was passed over the catalyst at atmospheric pressure (1 bar) at a flow rate of 50 ml/minute. Periodically, the effluent from the reactor was analyzed by gas chromatography (GC) to determine the product composition. The selectivity has been defined by the division of the mass of product i by the sum of the masses of all products. Table 1 lists the process parameters and the composition of the product, as determined by GC. The reactions of cyclopentene and dimethylether to the several methylcyclopentenes are exotherm. For example, the reaction of cyclopentene and dimethylether to 1-methylcyclopentene generates 54.4 kJ/mol.

TABLE 1

Process parameters and composition of the product

|  | MFI 280 | MTT 47 |
|---|---|---|
| Time on stream, hours | ~20 | ~20 |
| Temperature ° C. | 400° C. | 400° C. |
| CP conversion, % | 74 | 68 |
| DME conversion, % | 100 | 100 |
| Ethylene, selectivity, % | 6.0 | 1.4 |
| Propylene, selectivity, % | 22.9 | 6.7 |
| Butene isomers, selectivity, % | 17.0 | 5.8 |
| Pentene isomers, Selectivity, % | 10.7 | 7.8 |
| 1-Methylcyclopentene, selectivity, % | 9.5 | 39.3 |
| C6 isomers*, selectivity, % | 3.9 | 15.4 |
| C7 isomers**, Selectivity, % | 27.9 | 23.2 |
| Benzene, selectivity, % | 2.1 | 0.4 |

*excluding 1-methylcyclopentene and benzene, and consists of mostly other methylcyclopentenes.
**C7 isomers are dimethylcyclopentenes As can be seen from the above the process of the invention can advantageously generate a product composition comprising more than 10 wt % 1-methylcycloalkenes and less than 2 wt % benzenes.

What is claimed is:

1. A process for the alkylation of a cycloalkene, which process comprises alkylating a cycloalkene selected from the group consisting of cyclopentene, cyclohexene, ethylcyclohexene and vinyl-cyclohexene with an oxygenate under alkylating conditions in the presence of a zeolite chosen from the group consisting of TON, MTT, EUO, and EU-2 zeolites having a Silica to Alumina ratio in the range from 1 to 500 to yield an alkylated cycloalkene.

2. The process according to claim 1, wherein the oxygenate is methanol or dimethylether.

3. The process according to claim 1, wherein the zeolite is a MTT zeolite.

4. The process according to claim 1, wherein the zeolite has a silica to alumina ratio in the range from 10 to 200.

5. The process according to claim 1, wherein organic starting compound is contacted with the zeolite at a temperature in the range from 200° C. to 500° C., and at an absolute pressure in the range from 1 to 5 bar.

6. The process according to claim 1, wherein the cycloalkene is cyclopentene which is obtained by cracking dicyclopentadiene to cyclopentadiene and subsequently partly hydrogenating the cyclopentadiene to cyclopentene.

7. A process for the preparation of alkylated cyclopentenes which process comprises the steps of
   a) partial hydrogenation of a C5 distillation fraction of a pyrolysis gasoline, which fraction comprises cyclopentadienes, to obtain a partially hydrogenated C5 fraction, comprising cyclopentenes and cyclopentanes;
   b) catalytically cracking the C5 fraction obtained in step a), to obtain a cracked C5 fraction, comprising an increased amount of cyclopentenes;
   c) contacting the cracked C5 fraction obtained in step b) with an oxygenate under alkylating conditions in the presence of a zeolite chosen from the group consisting of TON, MTT, EUO, and EU-2 zeolites having a Silica to Alumina ratio in the range from 1 to 500 to obtain a mixture comprising alkylated cyclopentenes and other C5 compounds; and
   d) separating the alkylated cyclopentenes from the mixture obtained in step c).

* * * * *